(12) United States Patent
Sheth et al.

(10) Patent No.: US 9,586,040 B2
(45) Date of Patent: Mar. 7, 2017

(54) VACUUM-ACTUATED PERCUTANEOUS INSERTION/IMPLANTATION TOOL FOR FLEXIBLE NEURAL PROBES AND INTERFACES

(71) Applicants: Heeral Sheth, Oakland, CA (US); William J. Bennett, Livermore, CA (US); Satinderpall S. Pannu, Pleasanton, CA (US); Angela C. Tooker, Dublin, CA (US)

(72) Inventors: Heeral Sheth, Oakland, CA (US); William J. Bennett, Livermore, CA (US); Satinderpall S. Pannu, Pleasanton, CA (US); Angela C. Tooker, Dublin, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 726 days.

(21) Appl. No.: 13/898,385

(22) Filed: May 20, 2013

(65) Prior Publication Data

US 2014/0012284 A1    Jan. 9, 2014

Related U.S. Application Data

(60) Provisional application No. 61/649,175, filed on May 18, 2012.

(51) Int. Cl.
| | |
|---|---|
| *A61B 19/00* | (2006.01) |
| *A61N 1/05* | (2006.01) |
| *A61B 5/00* | (2006.01) |
| *A61B 5/04* | (2006.01) |

(52) U.S. Cl.
CPC ........ *A61N 1/0539* (2013.01); *A61B 5/04001* (2013.01); *A61B 5/685* (2013.01); *A61N 1/0531* (2013.01)

(58) Field of Classification Search
CPC .... A61N 1/0539; A61N 1/0531; A61N 1/053; A61B 5/04001; A61B 5/685; A61B 5/0478
USPC ................. 606/129; 600/377, 378; 607/116
See application file for complete search history.

(56) References Cited

U.S. PATENT DOCUMENTS

| | | | | |
|---|---|---|---|---|
| 4,919,129 A | * | 4/1990 | Weber, Jr. .......... | A61B 18/1402 604/35 |
| 5,035,695 A | * | 7/1991 | Weber, Jr. .......... | A61B 18/1402 604/35 |
| 5,055,100 A | * | 10/1991 | Olsen .................... | A61B 18/00 604/19 |
| 5,361,760 A | * | 11/1994 | Normann ............ | A61B 5/04001 600/377 |

(Continued)

OTHER PUBLICATIONS

O'Brien, et al., "Flexible Microelectrode Arrays with Integrated Insertion Devices", IEEE, pp. 216-218 (2001).

(Continued)

*Primary Examiner* — Amy R Weisberg
(74) *Attorney, Agent, or Firm* — James S. Tak

(57) ABSTRACT

A flexible device insertion tool including an elongated stiffener with one or more suction ports, and a vacuum connector for interfacing the stiffener to a vacuum source, for attaching the flexible device such as a flexible neural probe to the stiffener during insertion by a suction force exerted through the suction ports to, and to release the flexible device by removing the suction force.

5 Claims, 6 Drawing Sheets

(56) References Cited

U.S. PATENT DOCUMENTS

| | | | | | |
|---|---|---|---|---|---|
| 6,304,785 | B1* | 10/2001 | McCreery | ............ | A61N 1/0541 128/899 |
| 7,754,936 | B2* | 7/2010 | Heaton | ............. | A61F 13/00021 602/3 |
| 8,226,661 | B2* | 7/2012 | Balling | ................ | A61N 1/0551 606/129 |
| 8,479,354 | B1* | 7/2013 | Doyle | .................... | A47L 7/009 15/339 |
| 9,084,605 | B2* | 7/2015 | Hawkins | ............ | A61B 17/0469 |
| 2001/0011156 | A1* | 8/2001 | Viola | ................ | A61B 10/0275 600/568 |
| 2003/0055373 | A1* | 3/2003 | Sramek | ................ | A61B 10/025 604/19 |
| 2005/0177220 | A1* | 8/2005 | Iaizzo | .................... | A61B 5/042 607/126 |
| 2005/0238312 | A1* | 10/2005 | Meder | .................... | C03C 8/245 385/137 |
| 2007/0156126 | A1* | 7/2007 | Flaherty | ............... | A61B 5/0084 606/32 |
| 2007/0185502 | A1* | 8/2007 | Smits | .................. | A61N 1/3622 606/129 |
| 2008/0030121 | A1* | 2/2008 | Iwama | .................. | H01J 61/305 313/485 |
| 2008/0103577 | A1* | 5/2008 | Gerber | ................. | A61N 1/0529 607/149 |
| 2008/0221589 | A1* | 9/2008 | Balling | ................ | A61N 1/0551 606/129 |
| 2009/0155918 | A1* | 6/2009 | Payen | ................ | A61B 5/14539 436/149 |
| 2009/0312770 | A1* | 12/2009 | Kozai | .................. | A61B 5/6846 606/129 |
| 2010/0023021 | A1* | 1/2010 | Flaherty | ............... | A61B 5/0084 606/130 |
| 2010/0168761 | A1* | 7/2010 | Kassab | ................. | A61M 25/00 606/129 |
| 2010/0331935 | A1* | 12/2010 | Tabada | .................... | A61N 1/05 607/116 |
| 2011/0105952 | A1* | 5/2011 | Bernstein | ............... | A61B 5/157 600/573 |
| 2011/0130744 | A1* | 6/2011 | Kassab | .............. | A61B 17/0057 604/508 |
| 2013/0268041 | A1* | 10/2013 | Schulte | ................ | A61N 1/0558 607/117 |
| 2013/0320273 | A1* | 12/2013 | Kotov | ...................... | A61N 1/05 252/511 |
| 2014/0378993 | A1* | 12/2014 | Shah | .................... | A61N 1/0551 606/129 |

OTHER PUBLICATIONS

Lee, et al., "Polymide-based intracortical neural implant with improved structural stiffness", J. Micromech. Microeng. 14, pp. 32-37 (2004).

Foley, et al., "Flexible microfluidic devices supported by biodegradable insertion scaffolds for convection-enhanced neural drug delivery", Biomed Microdevices, 11, pp. 915-924 (2009).

Kozai, et al., "Insertion shuttle with carboxyl terminated self-assemled monolayer coatings for implanting flexible polymer neural probes in the brain", Journal of Neuroscience Methods, 184, pp. 199-205 (2009).

Jaroch, et al., "Magnetic insertion system for flexible electrode implantation", Journal of Neuroscience Methods, 183, pp. 213-222 (2009).

Lewitus, et al., "Ultrafast resorbing polymers for use as carriers for cortical neural probes", Acta Biomaterialia, 7, pp. 2483-2491 (2011).

* cited by examiner

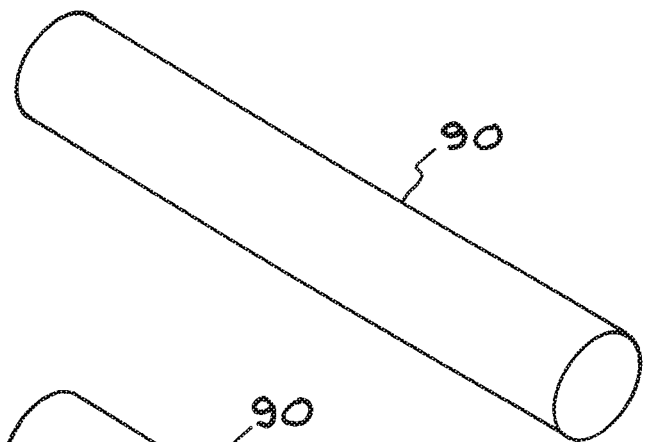
FIG. 11A
FIG. 11B
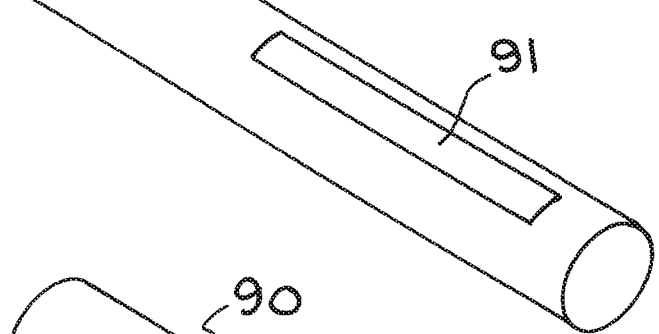
FIG. 11C
FIG. 11D

US 9,586,040 B2

VACUUM-ACTUATED PERCUTANEOUS INSERTION/IMPLANTATION TOOL FOR FLEXIBLE NEURAL PROBES AND INTERFACES

CLAIM OF PRIORITY IN PROVISIONAL APPLICATION

This patent document claims the benefit and priority of U.S. Provisional Application No. 61/649,175, filed on May 18, 2012, hereby incorporated by reference.

FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to flexible neural probes and interfaces, and more particularly to a vacuum-actuated insertion tool for percutaneous insertion or implantation of flexible neural probes and other flexible devices which are not sufficiently rigid to penetrate a percutaneous region unassisted.

BACKGROUND OF THE INVENTION

Microelectrode neural probes and interfaces are an essential tool in neuroscience. They typically comprise a multi-electrode array (MEA) configuration with exposed metal pads or electrodes located on rigid silicon shanks and connected, via interconnection traces, to output leads or to signal processing circuitry on a monolithic substrate. The exposed metal pads/electrodes provide a direct electrical interface with the neurons of a biological entity's nervous system to stimulate and/or record neural activity. Such neural probes can target the neuronal activity of neurons, enabling researchers and clinicians to better explore and understand neurological diseases, neural coding, neural modulations, and neural topologies, as well as treat debilitating conditions of the nervous system. Moreover, the ability to analyze neuronal activity using neural probes has led to the development of new neuro-therapeutic devices implemented through brain-machine interfaces. These interfaces use neural probes implanted to bypass damaged tissue and stimulate neural activity, so that a patient can regain lost communication and/or control with respect to some aspect of the patient's nervous system. Implantable neural probes and interfaces in particular enable extended interaction with neural tissue.

The flexibility of polymer-based intracortical neural implants provide an attractive alternative over conventional silicon-based neural probes and interfaces for reliable and stable long-term recording, stimulation, and/or monitoring of neuronal activities in the brain. Such flexible MEA probes are typically fabricated using multiple layers of polymers (e.g. biocompatible polymers such as polyimide, Parylene-C, and polyurethanes) coated layer by layer after each metal film deposition and patterning, to insulate the patterned conductive wiring and lines. The resulting electrode array is completely flexible and may enable extended interaction with neural tissue by mitigating the risk of silicon breakage and minimizing potential tissue damage caused by micro-motion between the brain and the implant, for long-term safety and functional stability.

However, the low mechanical stiffness of flexible polymer-based MEAs can cause bending or buckling when percutaneously penetrated/inserted into tissue, e.g. the pial membrane of the brain. In particular, the viscoelastic and inhomogeneous properties of the brain make the mechanics of probe insertion a complex problem with direct insertion difficult.

What is needed therefor is an insertion tool and method for percutaneously inserting/implanting flexible devices by providing adequate stiffness to the flexible device to enable tissue penetration and insertion.

SUMMARY OF THE INVENTION

One aspect of the present invention includes a flexible device insertion tool, comprising: a rigid-body shank having a handle end and an opposite insertion end, a suction channel extending between the handle and insertion ends, at least one suction port(s) in fluidic communication with the suction channel, and a connector port at the handle end in fluidic communication with the at least one suction port(s) via the suction channel; and a vacuum connector having a first port adapted to connect to a vacuum source, a second port in fluidic communication with the first port, and means for mounting the rigid-body shank on the vacuum connector so that the connector port of the rigid-body shank is aligned with the second port, and the first port is in fluidic communication with the at least one suction port(s), whereby, upon connecting a vacuum source to the first port, mounting the rigid-body shank on the vacuum connector, and activating the vacuum source, a flexible device positioned adjacent the at least one suction port(s) is releasably attached to the rigid-body shank by a suction force exerted by the at least one suction port(s) during insertion.

Another aspect of the present invention includes a flexible device insertion tool, comprising: a vacuum connector section having a connector port adapted to fluidically connect to a vacuum source; and an elongated rigid-body shank section connected to and extending from the vacuum connector section to an insertion end, said elongated rigid-body shank section having a suction channel in fluidic communication with the connector port and extending to the insertion end, and at least one suction port(s) in fluidic communication with the connector port via the suction channel, whereby, upon connecting a vacuum source to the connector port of the vacuum connector section and activating the vacuum source, a flexible device positioned adjacent the at least one suction port(s) is releasably attached to the rigid-body shank section by a suction force exerted by the at least one suction port(s) during insertion.

Another aspect of the present invention includes a rigid-body shank for inserting a flexible device, comprising: an elongated shank body having a handle end and an opposite insertion end, a suction channel extending between the handle and insertion ends, at least one suction port(s) in fluidic communication with the suction channel, and a connector port at the handle end in fluidic communication with the at least one suction port(s) via the suction channel and adapted to fluidically connect to a vacuum source, whereby, upon connecting a vacuum source to the connector port and activating the vacuum source, a flexible device positioned adjacent the at least one suction port(s) is releasably attached to the shank body by a suction force exerted by the at least one suction port(s) during insertion.

Another aspect of the present invention includes a vacuum connector for flexible device insertion tools, comprising: a connector body having a first port adapted to connect to a vacuum source, a second port in fluidic communication with the first port, and means for mounting a rigid-body shank on the connector body so that a connector port of a suctioning system of the rigid-body shank is aligned with the second port, whereby upon connecting a vacuum source to the first port and activating the vacuum source, a suction force generated by the vacuum source may be transferred to a flexible device via the suctioning system of the rigid-body shank, to releasably attach the flexible device to the rigid-body shank during insertion.

Another aspect of the present invention includes a method of percutaneously inserting a flexible device, comprising: providing a rigid-body shank having a handle end and an opposite insertion end, a suction channel extending between the handle and insertion ends, at least one suction port(s) in fluidic communication with the suction channel, and a connector port at the handle end in fluidic communication with the at least one suction port(s) via the suction channel; providing a vacuum connector having a first port adapted to connect to a vacuum source, a second port in fluidic communication with the first port, and means for mounting the rigid-body shank on the vacuum connector so that the connector port of the rigid-body shank is aligned with the second port and the first port is in fluidic communication with the at least one suction port(s); mounting the rigid-body shank on the vacuum connector; positioning a flexible device adjacent the at least one suction port(s); connecting a vacuum source to the first port of the vacuum interface connector and activating the vacuum source to releasably attach the flexible device to the rigid-body shank by a suction force exerted by the at least one suction port(s); percutaneously inserting the rigid-body shank with the suction-attached flexible device; deactivating the vacuum source to release the flexible device from the rigid-body shank; and removing the rigid-body shank, leaving the flexible device remaining inserted.

And another aspect of the present invention includes a method of inserting a flexible device, comprising: providing a flexible device insertion tool having a vacuum interface connector section having a connector port adapted to fluidically connect to a vacuum source, and an elongated rigid-body shank section connected to and extending from the vacuum interface connector section to an insertion end, said elongated rigid-body shank section having a suction channel in fluidic communication with the connector port and extending to the insertion end, and at least one suction port(s) in fluidic communication with the connector port via the suction channel; positioning a flexible device adjacent the at least one suction port(s); connecting a vacuum source to the connector port of the vacuum interface connector section and activating the vacuum source to releasably attach the flexible device to the rigid-body shank section by a suction force exerted by the at least one suction port(s); percutaneoulsy inserting the rigid-body shank section with the suction-attached flexible device; deactivating the vacuum source to release the flexible device from the rigid-body shank section; and removing the rigid-body shank section, leaving the flexible device remaining inserted.

Generally, the present invention is directed to a vacuum-actuated, flexible device insertion tool and method which uses a vacuum source to temporarily attach a flexible device to a rigid shank of the insertion tool to provide the necessary stiffness to penetrate into neural tissue and insert or implant the flexible device therein, and which can be subsequently removed after insertion, leaving the flexible probe in place. In this manner, the present invention provides a mechanism of stiffening flexible polymer probes to assist with penetration in neural tissue, while also providing the ability to immediately remove the stiffener after the probe is positioned in place. Immediate removal of the stiffening shank helps to reduce surgery time as well as tissue inflammatory response. It is appreciated that the flexible device may be a MEA device having a generally flexible construction which makes percutaneous insertion difficult without assistance, and which may have various device shapes, number of metal layers, number of electrodes, etc. For example, the encapsulated MEA device may be a MEA neural probe or interface useful for a variety of applications in peripheral and cortical nerve stimulation and recording, including as a chronic, fully-implanted neural interface capable of extended operational lifetime due to reduced modes of failure through interface delamination.

In one example embodiment, the vacuum-actuated removable insertion tool comprises two main components: (1) a metal, silicon or polymer based stiffener with a suction channel in a rigid-body insertion shank of the stiffener that provides suctioning capability to a flexible probe; and (2) a vacuum connector that provides an interface between the stiffener and the vacuum source and provides a mounting structure for the stiffener if the stiffener is provided as an independent component. Generally, the stiffener is constructed of a sufficiently rigid material capable of withstanding multiple insertions and removals without buckling and breakage, i.e. having a buckling strength that is significantly greater than the force needed to penetrate that specific tissue and overcome the friction applied to the moving probe shank during insertion and removal. In another example embodiment, the flexible device insertion tool may be provided with the stiffener and vacuum connector connected as an integrated unit. In this case the tool includes a vacuum connector section having a connector port adapted to fluidically connect to a vacuum source, and an elongated rigid-body shank section connected to and extending from the vacuum connector section to an insertion end. The elongated rigid-body shank section has a suction channel in fluidic communication with the connector port and extends to the insertion end In operation, a flexible device may be positioned and aligned along the one or more suction ports of the stiffener, e.g. under a microscope. While the shank remains aligned, the vacuum source (which is connected to the vacuum connector) may be activated to produce in the channel a suction force against the flexible device, to pull and keep the device in place and in close contact with the stiffening shank during implantation. The vacuum connector and the stiffener together operate to apply a suction force to the flexible device to hold it in place during insertion. Upon percutaneously inserting the probe and placing it precisely within tissue, the vacuum pressure is disabled or deactivated, to remove the suction force and release the device from the stiffener. After detaching the flexible device, the stiffener may be removed from the tissue, leaving the flexible device remaining inserted or implanted. In this manner, the invention provides a simple and effective method of attaching an insertion scaffold to a flexible polymer probe using a vacuum source. The insertion scaffold can be immediately removed by releasing the vacuum once the probe is positioned in the tissue.

BRIEF DESCRIPTION OF THE DRAWINGS

The accompanying drawings, which are incorporated into and form a part of the disclosure, are as follows:

FIGS. 11A-D shows an alternative method of fabricating an insertion shank of the present invention similar to FIG. 10 without support ribs to form an open channel section with a single vacuum port.

DETAILED DESCRIPTION

Figure 1:
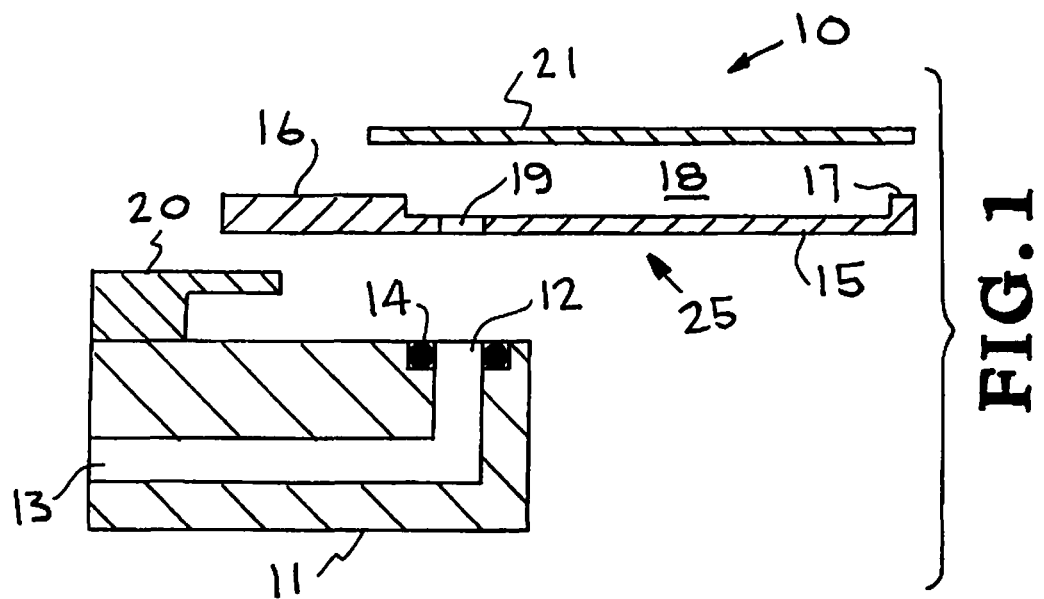
FIG. 1 is an exploded cross-sectional view of an example schematic embodiment of the flexible device insertion tool of the present invention having an open suction channel which may be used, for example, for percutaneous applications.
Figure 2:
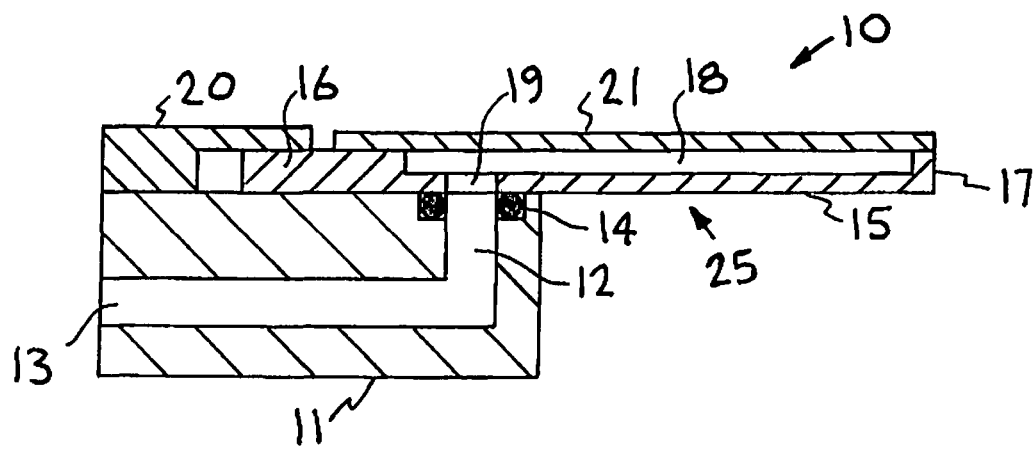
FIG. 2 is an assembled cross-sectional view of the example schematic embodiment of the flexible device insertion tool of FIG. 1.

Turning now to the drawings, FIGS. 1 and 2 show an example schematic embodiment of the flexible device insertion tool of the present invention, generally indicated at reference character 10, and comprising a rigid-body stiffener 25, and a vacuum connector 11 upon which the stiffener 25 may be mounted and secured to provide connection to a vacuum source (not shown). The insertion tool 10 is also shown with a flexible device 21 positioned against and temporarily connected to the stiffener 25 so as to be percutaneously insertable together with the stiffener.

Figure 3:
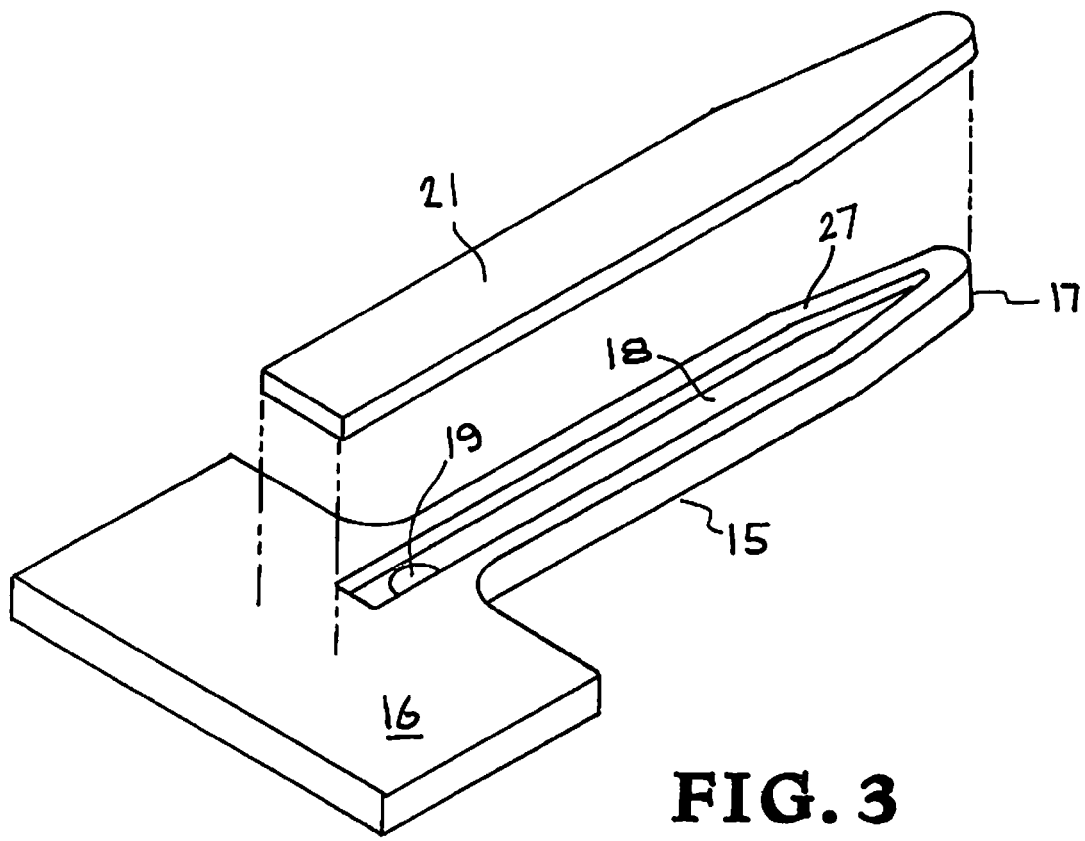
FIG. 3 is an exploded perspective view of a flexible device and an example embodiment of the stiffener of the present invention having an open suction channel.

As shown in FIGS. 1 and 2, the stiffener 25 has an elongated insertion shank 15, with a handle end 16, an opposite insertion end 17, and a channel 18 extending between the handle and insertion ends. In particular, the channel 18 is open on one side, with the opening forming a single elongated port along the side of the insertion shank. The stiffener also includes a connector port 19 that is in fluidic communication with the channel 18 and the single elongated port. FIG. 3 also shows a perspective view of the stiffener 25, illustrating the open channel 18 forming the single elongated suction port along the insertion shank 15. As can be seen in FIG. 3, the channel 18 is surrounded by a raised perimeter having a support surface 27 against which the device 21 contacts when positioned for insertion. The port 19 is also shown near the handle end 16 at the bottom of the channel 18. Traditional semi-conductor fabrication processes (e.g. photolithography, wet/dry/etch, etc.) may be used to fabricate the stiffener, such as for example fabricating the stiffener from a silicon-on-insulator (SOI) wafer.

Also in FIGS. 1 and 2, the vacuum connector 11 is shown having a fastener for mounting or otherwise connecting the stiffener 25 to the vacuum connector 11 so that the connector port 19 of the rigid-body shank 15 is aligned with one of the ports of the vacuum connector 12. Various types of fasteners may be used, such as for example various types of clamps (e.g. screw-in clamp), clips, screws, bolts, ties, for securing the stiffener to the vacuum connector. It is appreciated that the fastener 20 in FIGS. 1 and 2 may be removable from the body of the vacuum connector 11 to enable positioning of the stiffener 25 on the vacuum connector 11 first, followed by fastening (e.g. clamping) of the fastener 20 on the stiffener. In the alternative, the fastener may be adapted to securably receive the stiffener in a single motion, such as by a latching mechanism, or using a resiliently biasing arm and slidably securing the stiffener under said arm. It is also appreciated that the fastener may provide either a temporary connection, such that stiffeners may be removed and replaced, or a permanent connection, whereby the stiffener and vacuum source are considered an integrated unit. In this regard, adhesives may also be considered fasteners for connecting the stiffener to the vacuum connector. In the alternative the stiffening shank and vacuum support structure/connector may be otherwise integrated as a unitary structure (e.g. for single use). By separating the stiffener from vacuum connector, the stiffener may be discarded after use but the connector reused.

The vacuum connector 11 is also shown having first and second vacuum ports 12 and 13 respectively in fluidic communication with each other. The second vacuum port 13 is adapted to connect to a vacuum source, and the first vacuum port 12 is positioned so that when the stiffener 25 is connected to the vacuum connector 11, the first vacuum port 12 aligns with the port 19, and the open channel and the suction port of the stiffener is in fluidic communication with the vacuum source. Furthermore, when a flexible device such as 21 is positioned against the shank 15, a suction force is produced through the open port and against the device to attach the device to the stiffener. An O-ring 14 is also shown provided at the first port 12 to seal the interface between the port 19 and the first vacuum port 12 when the stiffener is secured to the vacuum connector. This particular design may be used, for example, for percutaneous applications where full implantation is not desired, since a portion of the inserted device will remain outside and exposed.

Figure 4:
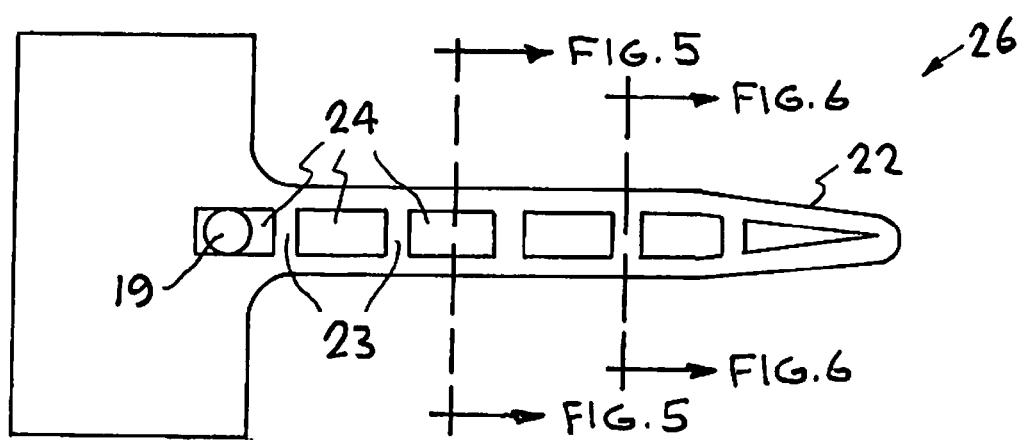
FIG. 4 is a top view of another example embodiment of the insertion shank of the present invention having support beams/ribs bridging the open suction channel.
Figure 5:
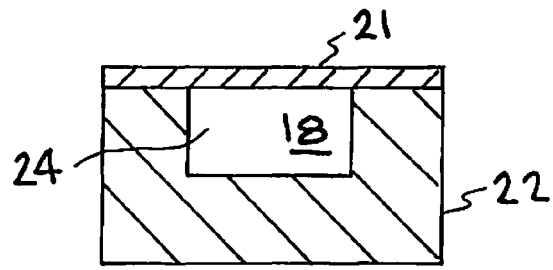
FIG. 5 is a cross-sectional view taken from FIG. 4 illustrating a section of the insertion shank without a support rib.
Figure 6:
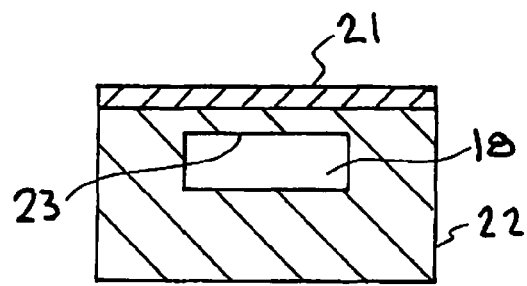
FIG. 6 is a cross-sectional view taken from FIG. 4 illustrating a section of the insertion shank with a support rib.

FIGS. 4-6 show an example embodiment of the stiffener 26 of the insertion tool of the present invention, having a similar general shape as the stiffener 25 of FIGS. 1-3 with an elongated insertion shank 22 along which a channel 18 is formed. In this embodiment, however, support ribs 23 are also provided and distributed along the channel 18 to provide additional support surfaces (similar to surfaces 27) against which the device 21 contacts when positioned for insertion. Moreover, the support ribs 23 form multiple suction ports 24, each of which exerts a vacuum/suction force against a device positioned thereagainst, and the support ribs 23 help maintain a planar orientation of the device. It is appreciated that the support ribs 23 may be formed using traditional semi-conductor fabrication processes (e.g. photolithography, wet/dry/etch, etc.) as discussed for the stiffener of FIGS. 1 and 2. In the alternative it is appreciated that the ribs may be formed, for example, using two SOIs, as described for the embodiment of FIGS. 7 and 8. In the case of FIG. 8, support ribs may be formed on the top shank 50 prior to being bonded or otherwise attached to the bottom shank.

Figure 7:
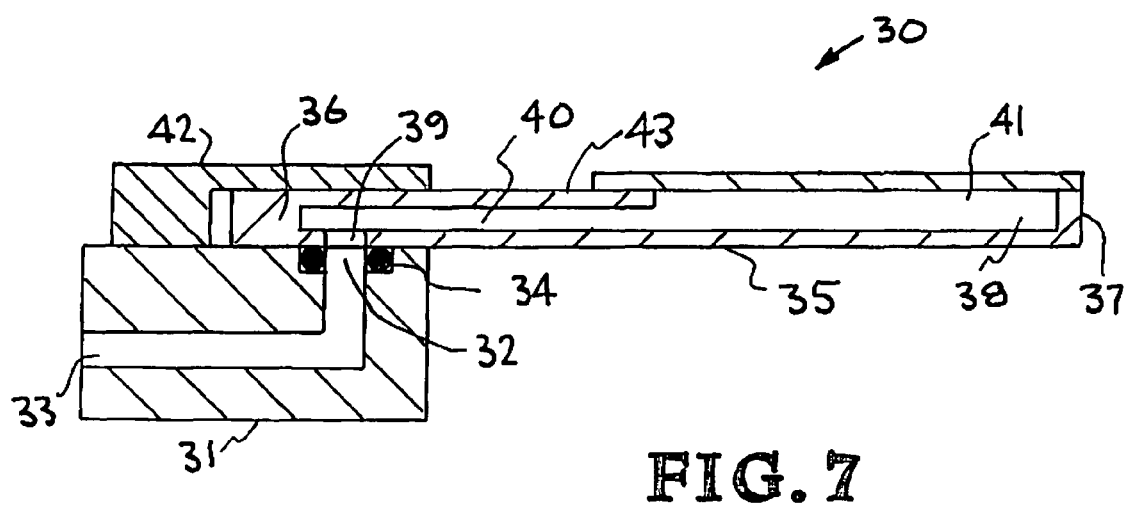
FIG. 7 is an assembled cross-sectional view of another example schematic embodiment of the flexible device insertion tool of the present invention having a partially-enclosed suction channel which may be used, for example, for full implant applications.
Figure 8:
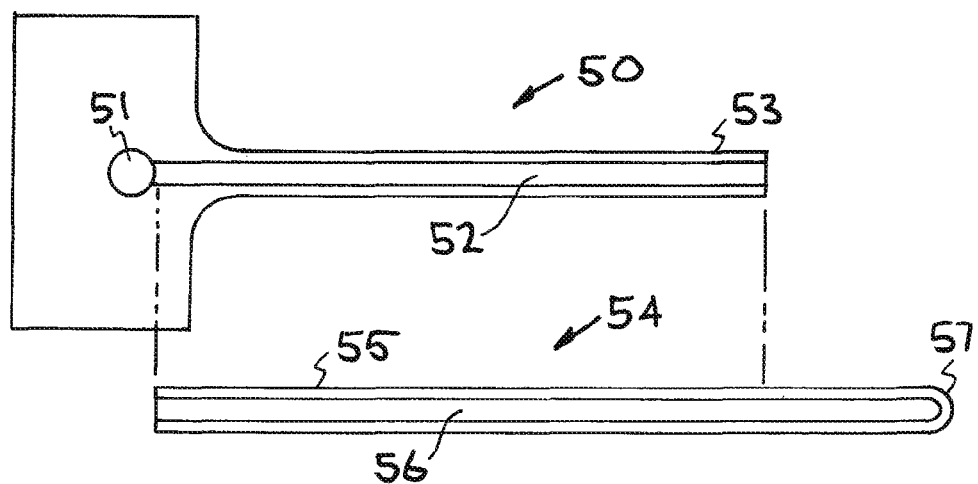
FIG. 8 shows plan views of the top and bottom portions of an example insertion shank having a partially-enclosed suction channel.

FIG. 7 shows another example embodiment of the flexible device insertion tool of the present invention generally indicated at reference character 30. Similar to FIGS. 1-3, the tool 30 includes a vacuum connector 31 having first and second vacuum ports 33, 32 in fluidic communication with each other, and a fastener 42 for temporarily or permanently securing a stiffener 43 to the vacuum connector. And an O-ring 34 is also shown for enhancing the connection with an attached stiffener.

In particular, the stiffener 43 is shown having an insertion shank 35 with a handle end 36, an insertion end 37 and a channel 38 extending between a port 39 and a suction port 41, and providing fluidic communication therebetween. The channel 38 includes an enclosed section 40 near the handle end 36, and an open section which forms the open port 41. As such, the channel 38 may be characterized as a partially-enclosed suction channel, which may be useful for inserting/implanting fully implanted devices because the enclosed section is necessary to deliver the vacuum force to the suction port 41 near the insertion end 37 to enable the depth of penetration and insertion necessary to fully implant the device in the tissue. Similar to the embodiment shown in FIGS. 1-3, traditional semi-conductor fabrication processes (e.g. photolithography, wet/dry/etch, etc.) may be used to fabricate the stiffener with partially-enclosed suction channel. For example, the stiffener with enclosed and open sections of the channel may be created using two SOI wafers to produce a top shank portion and a bottom shank portion separately, and subsequently joined (e.g. bonded) together. FIG. 8 illustrates an example top shank 50 and bottom shank 54 of such a stiffener fabricated according to such process. The top shank 50 is shown having a top shank channel 52 extending between a port 51 (for communicating with the vacuum connector) and an end 53. And the bottom shank 54 is shown having a bottom shank channel 56 extending between a first end 55 and a second end 57. When combined, the first end 55 is positioned adjacent the port 51 to enclose the channel from 55 to 53, which an open suction port is formed between 53 and the insertion end 57.

Figure 9:
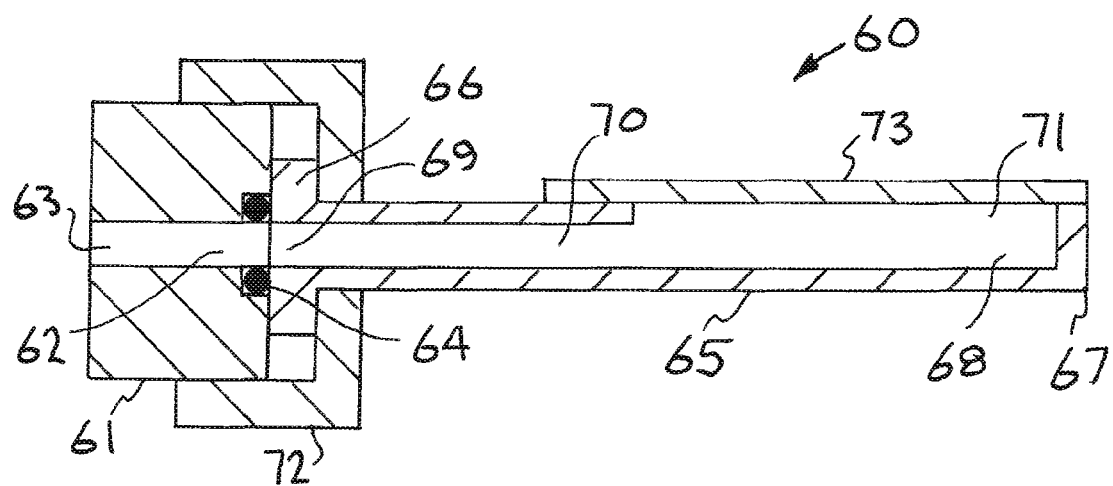
FIG. 9 shows an assembled cross-sectional view of another example schematic embodiment of the flexible device insertion tool of the present invention where the insertion shank and the support structure are connectable in an in-line arrangement.
Figure 10A:
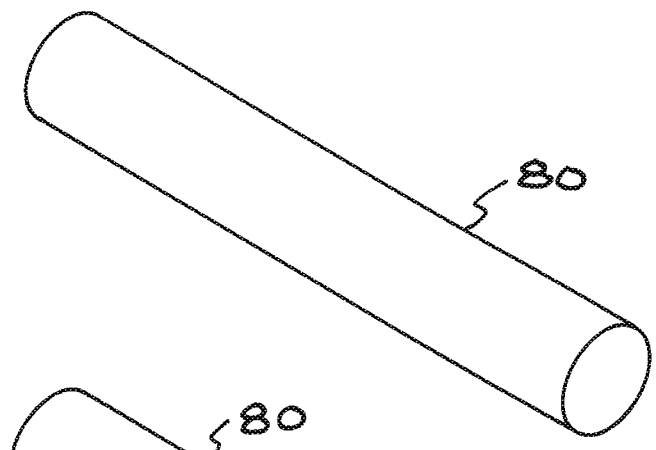
FIGS. 10A-D shows an alternative method of fabricating an insertion shank of the present invention with support ribs forming multiple suction ports.
Figure 10B:
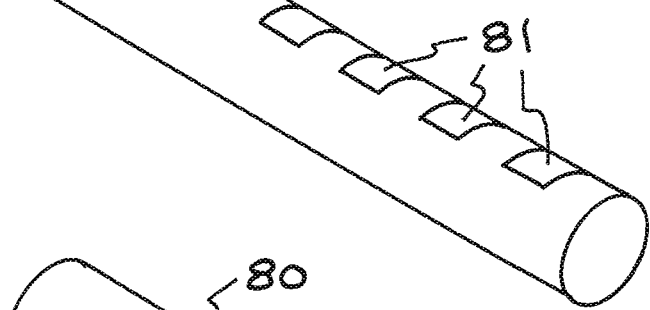
Figure 10C:
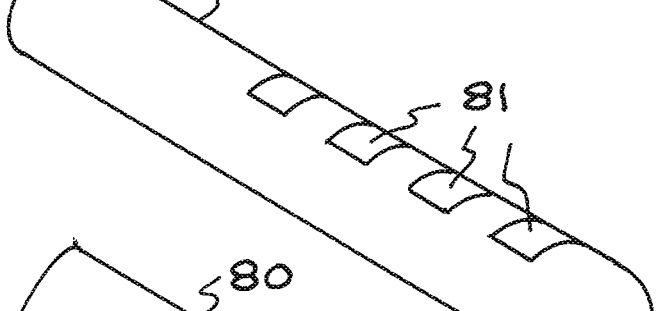
Figure 10D:
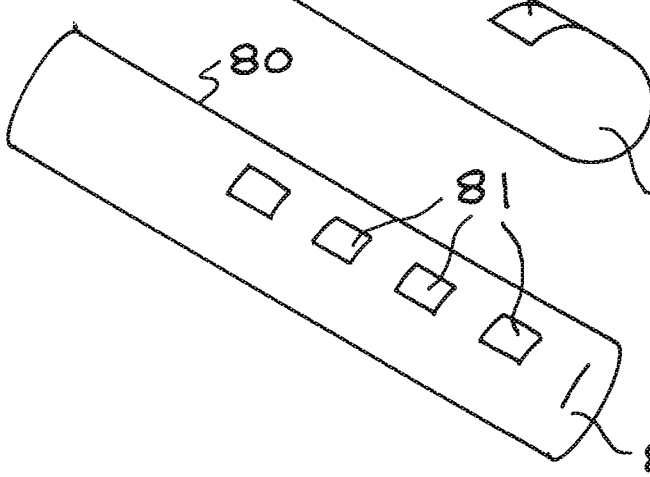

FIG. 9 shows another embodiment of the insertion tool of the present invention generally indicated at reference character 60, where the stiffener is adapted to connect in-line with the vacuum connector. In particular, the stiffener is shown having an elongated insertion shank 65 with a channel 68 extending between a handle end 66 and an insertion end 67, and enabling fluidic communication between port 69 and the suction port 71 where a device 73 is shown attached by vacuum suction. Similar to the embodiment of FIG. 7, the channel 68 includes an enclosed section 70 near the handle end 66, and an open section which forms the suction port 71. And the vacuum connector 61 is shown having a first vacuum port 62, and a second vacuum port 63 adapted to connect to a vacuum source (not shown). Moreover, the first and second ports 62, 63 and the port 69 of the stiffener are arranged in-line along a longitudinal axis of the stiffener. A fastener 72, as previously described for other embodiments, is also shown for securing the stiffener to the vacuum connector in the inline arrangement. And an O-ring 64 is also shown providing a seal between the first port 62 and the port 69.

And FIGS. 10A-D and 11A-D show alternate example embodiments of the insertion tool and fabrication methods thereof of the present invention. In particular, FIGS. 10A-D shows the progression of steps, and starting with a tubular structure 80 made of a material with a suitably high Young's Modulus, which may be, for example, hollow metal wire (e.g. tungsten, chromium, gold, iridium, titanium), micro-hypodermic needles, biocompatible polymers, ceramics (e.g. sapphire, alumina, silicon carbide, titanium-nitride, tungsten carbide, zirconium carbide, zirconium nitride) and sheet metal alloys. A linear array of slots or apertures 81 is shown formed (e.g. laser cut) on one side of the tubular structure 80 adjacent one end, with that end being subsequently capped at 82 (e.g. by heating the end about the material's melting temperature) to form a closed seal so that the suction force is only applied through the slots. The entire tubular structure 80 is then flattened so that the array of apertures is positioned on one side of the flattened structure. Similarly, in FIGS. 11A-D, a tubular structure 90 is shown provided and formed with a single elongated aperture 91 on one side of the structure. An end cap 82 is also formed to close off the end near the aperture, followed by flattening of the structure 90 with the single aperture positioned on one side of the flattened structure.

While particular operational sequences, materials, temperatures, parameters, and particular embodiments have been described and or illustrated, such are not intended to be limiting. Modifications and changes may become apparent to those skilled in the art, and it is intended that the invention be limited only by the scope of the appended claims.

We claim:
1. A flexible device insertion tool, comprising:
a linear rigid-body shank having a handle end and an opposite insertion end, a suction channel extending between the handle and insertion ends, suction ports located between the handle and insertion ends and in fluidic communication with the suction channel, and a connector port at the handle end in fluidic communication with the suction ports via the suction channel; and
a vacuum connector having a first port adapted to connect to a vacuum source, a second port in fluidic communication with the first port, and means for mounting the handle end of the rigid-body shank on the vacuum connector so that the connector port of the rigid-body shank is aligned with the second port, and the first port is in fluidic communication with the suction ports,
whereby, upon connecting a vacuum source to the first port, mounting the rigid-body shank on the vacuum connector, and activating the vacuum source, an elongated flexible device positioned adjacent the suction ports is releasably attached alongside and parallel to the rigid-body shank by a suction force exerted by the suction ports during insertion,
wherein the rigid-body shank includes support ribs distributed along the suction channel so that the suction ports are formed therebetween.
2. A flexible device insertion tool, comprising:
a vacuum connector section having a connector port adapted to fluidically connect to a vacuum source; and
an elongated linear rigid-body shank section connected to and extending from the vacuum connector section to an insertion end, said elongated rigid-body shank section having a suction channel in fluidic communication with the connector port and extending to the insertion end, and suction ports located between the vacuum connector section and the insertion end and in fluidic communication with the connector port via the suction channel, whereby, upon connecting a vacuum source to the connector port of the vacuum connector section and activating the vacuum source, an elongated flexible device positioned adjacent the suction ports is releasably attached alongside and parallel to the rigid-body shank section by a suction force exerted by the suction ports during insertion, wherein the rigid-body shank section includes support ribs distributed along the suction channel so that the suction ports are formed therebetween.

3. A rigid-body shank for inserting a flexible device, comprising:

an elongated linear rigid shank body having a handle end and an opposite insertion end, a suction channel extending between the handle and insertion ends, suction ports located between the handle end and the insertion end and in fluidic communication with the suction channel, and a connector port at the handle end in fluidic communication with the suction ports via the suction channel and adapted to fluidically connect to a vacuum source, whereby, upon connecting a vacuum source to the connector port and activating the vacuum source, an elongated flexible device positioned adjacent the suction ports is releasably attached alongside and parallel to the shank body by a suction force exerted by the suction ports during insertion, wherein the shank body includes support ribs distributed along the suction channel so that the suction ports are formed therebetween.

4. A method of percutaneously inserting a flexible device, comprising:

providing a linear rigid-body shank having a handle end and an opposite insertion end, a suction channel extending between the handle and insertion ends, suction ports located between the hand end and the insertion end and in fluidic communication with the suction channel, and a connector port at the handle end in fluidic communication with the suction ports via the suction channel;

providing a vacuum connector having a first port adapted to connect to a vacuum source, a second port in fluidic communication with the first port, and means for mounting the rigid-body shank on the vacuum connector so that the connector port of the rigid-body shank is aligned with the second port and the first port is in fluidic communication with the suction ports;

mounting the rigid-body shank on the vacuum connector;

positioning an elongated flexible device adjacent the suction ports;

connecting a vacuum source to the first port of the vacuum interface connector and activating the vacuum source to releasably attach the flexible device alongside and parallel to the rigid-body shank by a suction force exerted by the suction ports;

percutaneously inserting the rigid-body shank with the suction-attached flexible device;

deactivating the vacuum source to release the flexible device from the rigid-body shank;

removing the rigid-body shank, leaving the flexible device remaining inserted; and wherein the rigid-body shank includes support ribs distributed along the suction channel so that the suction ports are formed therebetween.

5. A method of inserting a flexible device, comprising:

providing a flexible device insertion tool having a vacuum interface connector section having a connector port adapted to fluidically connect to a vacuum source, and an elongated linear rigid-body shank section connected to and extending from the vacuum interface connector section to an insertion end, said elongated rigid-body shank section having a suction channel in fluidic communication with the connector port and extending to the insertion end, and suction ports located between the connector port and the insertion end and in fluidic communication with the connector port via the suction channel;

positioning a flexible device adjacent the suction ports;

connecting a vacuum source to the connector port of the vacuum interface connector section and activating the vacuum source to releasably attach the flexible device alongside and parallel to the rigid-body shank section by a suction force exerted by the suction ports;

percutaneously inserting the rigid-body shank section with the suction-attached flexible device;

deactivating the vacuum source to release the flexible device from the rigid-body shank section;

removing the rigid-body shank section, leaving the flexible device remaining inserted; and wherein the rigid-body shank section includes support ribs distributed along the suction channel so that the suction ports are formed therebetween.

\* \* \* \* \*